(12) United States Patent
Ogawa

(10) Patent No.: US 10,219,997 B2
(45) Date of Patent: Mar. 5, 2019

(54) RADIATION SENSITIZER OR ANTI-CANCER CHEMOTHERAPY SENSITIZER

(75) Inventor: Yasuhiro Ogawa, Nankoku (JP)

(73) Assignee: KOCHI UNIVERSITY, Kochi (JP)

(*) Notice: Subject to any disclaimer, the term of this patent is extended or adjusted under 35 U.S.C. 154(b) by 0 days.

(21) Appl. No.: 12/311,185

(22) PCT Filed: Sep. 21, 2007

(86) PCT No.: PCT/JP2007/068376
§ 371 (c)(1),
(2), (4) Date: Mar. 20, 2009

(87) PCT Pub. No.: WO2008/041514
PCT Pub. Date: Apr. 10, 2008

(65) Prior Publication Data
US 2010/0010417 A1 Jan. 14, 2010

(30) Foreign Application Priority Data
Sep. 22, 2006 (JP) .................. 2006-257703

(51) Int. Cl.
*A01N 39/00* (2006.01)
*A61K 9/00* (2006.01)
(Continued)

(52) U.S. Cl.
CPC .......... *A61K 9/0009* (2013.01); *A61K 9/0019* (2013.01); *A61K 31/728* (2013.01);
(Continued)

(58) Field of Classification Search
CPC .. A61K 9/0019; A61K 31/715; A61K 31/728; A61K 33/40; A61K 47/36; A61N 5/10; A61N 5/103
See application file for complete search history.

(56) References Cited

U.S. PATENT DOCUMENTS

| | | |
|---|---|---|
| 4,946,780 A | 8/1990 | Hashimoto et al. |
| 5,638,787 A | 6/1997 | Riordan et al. |

(Continued)

FOREIGN PATENT DOCUMENTS

| | | |
|---|---|---|
| CA | 2 122 519 | 10/1995 |
| CN | 1151118 | 6/1997 |

(Continued)

OTHER PUBLICATIONS

Hecht JR et al. Clin. Cancer Res. 2003; 9: 555-561.*

(Continued)

*Primary Examiner* — David Browe
(74) *Attorney, Agent, or Firm* — Christensen O'Connor Johnson Kindness PLLC

(57) ABSTRACT

The present invention provides a novel radiosensitizer or anti-cancer chemotherapy sensitizer. In particular, the invention provides a radiosensitizer or anti-cancer chemotherapy sensitizer that can relieve the irritation of an affected area caused by hydrogen peroxide, is safe when injected into a human body, and can delay or reduce the degradation of hydrogen peroxide and thereby can efficiently exert a radiation sensitizing effect and an anti-cancer chemotherapy sensitizing effect. The radiosensitizer or anti-cancer chemotherapy sensitizer comprises a combination of (a) hydrogen peroxide and (b) hyaluronic acid or salt thereof.

8 Claims, 6 Drawing Sheets

(51) Int. Cl.
*A61K 31/728* (2006.01)
*A61K 33/40* (2006.01)
*A61K 41/00* (2006.01)
*A61K 45/06* (2006.01)
*A61K 9/06* (2006.01)

(52) U.S. Cl.
CPC .......... *A61K 33/40* (2013.01); *A61K 41/0038* (2013.01); *A61K 45/06* (2013.01); *A61K 9/06* (2013.01)

(56) References Cited

U.S. PATENT DOCUMENTS

| | | | |
|---|---|---|---|
| 5,639,787 A * | 6/1997 | Riordan et al. | 514/474 |
| 5,676,964 A | 10/1997 | Della Valle et al. | |
| 6,387,413 B1 | 5/2002 | Miyata et al. | |
| 6,790,461 B2 | 9/2004 | Miyata et al. | |
| 6,825,186 B1 * | 11/2004 | Sessler et al. | 514/185 |
| 7,014,860 B1 | 3/2006 | Kawata et al. | |
| 2004/0086453 A1 * | 5/2004 | Howes | 424/1.11 |
| 2006/0178342 A1 | 8/2006 | Brown et al. | |
| 2006/0251719 A1 | 11/2006 | Tabata | |
| 2006/0263395 A1 | 11/2006 | Brown et al. | |
| 2009/0074879 A1 | 3/2009 | Braguti et al. | |
| 2009/0269404 A1 | 10/2009 | Ishiguro et al. | |

FOREIGN PATENT DOCUMENTS

| | | | |
|---|---|---|---|
| EP | 0 341 745 | 12/1994 | |
| JP | 63-123392 | 5/1988 | |
| JP | 1-266102 | 10/1989 | |
| JP | 2-234689 | 9/1990 | |
| JP | 2003-252905 | 9/2003 | |
| JP | 2004-203829 | 7/2004 | |
| JP | 2004-277348 | 10/2004 | |
| JP | 2005-325075 | 11/2005 | |
| UA | 16 358 | 8/2006 | |
| WO | WO 94/20115 | * 9/1994 | A61K 31/725 |
| WO | 99/10385 | 3/1999 | |
| WO | 01/57093 | 8/2001 | |
| WO | 2007/017176 | 2/2007 | |
| WO | 2008/016163 | 2/2008 | |
| WO | 2009/075329 A1 | 6/2009 | |
| WO | 2009/116556 A1 | 9/2009 | |

OTHER PUBLICATIONS

International Search Report dated Nov. 20, 2007 in the International (PCT) Application PCT/JP2007/068376 of which the present application is the U.S. National Stage.
Yasuhiro Ogawa et al., Apoptotic-resistance of the human osteosarcoma cell line HS-Os-1 to irradiation is converted to apoptotic-susceptibility by hydrogen peroxide: A potent role of hydrogen peroxide as a new radiosensitizer, Int'l J. of Molecular Med., 2003, vol. 12, pp. 845-850.
Yasuhiro Ogawa et al., Mechanism of hydrogen peroxide-induced apoptosis of the human osteosarcoma cell line HS-Os-1, Int'l J. of Molecular Med., 2003, vol. 12, pp. 459-463.
Merck Index 11th edition, 1989, pp. 760-761.
Eiichi Fujihira et al., Kobunshi Hyaluronic Acid Sodium (NRD101) no Chintsu, Koensho Sayo, Basic Pharmacology & Therapeutics, 1994, vol. 22, No. 3, pp. S703-S715 and the English Abstract thereof.
Hajime Yamamoto et al., Shokuyo Hyaluronic Acid (ECM-E) no Chintsu Sayo oyobi Sosho Chiryo Sokusyhin Koka, Medicine and Biology, 1999, vol. 139, No. 6, pp. 253-258 and partial English translation.
Theodore L. Phillips, Chemical Modifiers of Cancer Treatment, Int. J. Radiation Oncology Biol. Phys., 1984, vol. 10 pp. 1791-1794.
C. Norman Coleman, Hypoxic Cell Radiosensitizers: Expectations and Progress in Drug Development, Int. J. Radiation Oncology Biol. Phys., 1985, vol. 11, pp. 323-329.
Eric. J. Hall et al., Radiobiology for the Radiologist (Sixth Ediction), 2006, pp. 419-431.
Yasuhiro Ogawa et al., Mechanism of apoptotic resistance of human osteosarcoma cell line, HS-Os-1, against irradiation, Int'l , J. of Molecular Med., 2003, vol. 12, pp. 453-358.
Yasuhiro Ogawa et al., Immunocytochemical characeristics of human osteosarcoma cell line HS-Os-1: Possible implication in apoptotic resistance against irradiation, Int'l J. of Molecular Med., 2004, vol. 14, pp. 397-403.
Renato Toffanin et al., NMR studies of oligosaccharides derived from hyaluronate: complete assignment of $^1$H and $^{13}$C NMR spectra of aqueous di- and tetra-saccharides, and comparison of chemical shifts for oligosaccharides of increasing degree of polymerisation, Carbohydrate Research, 1993, vol. 245, pp. 113-128.
Mary K. Cowman et al., $^{13}$C-N Studies of Hyaluronan: Conformational Sensitivity to Varied Environments, Macromolecules, 1996, vol. 29, pp. 2894-2902.
John R. Haaga et al., Combined Tumor Therapy by Using Radiofrequency Ablation and 5-FU-Laden Polymer Implants: Evaluation in Rats and Rabbits, Radiology, 2005, vol. 237, pp. 911-918.
Chikako Yomota, Evaluation of Molecular Weights of Hyaluronate Preparations by Multi-Angle Laser Light Scattering, Bull. Natl. Inst. Health Sci., 2003, vol. 121, pp. 030-033 and the English Abstract thereof.
International Search Report dated May 13, 2014 in related Application No. PCT/JP2014/053542.
Masaya Yamamoto et al., "Controlled release by biodegradable hydrogels enhances the ectopic bone formation of bone morphogenetic protein", Biomaterials, vol. 24, p. 4375-4383 (2003).
Yasuhiro Ogawa et al., "Phase I study of a new radiosensitizer containing hydrogen peroxide and sodium hyaluronate for topical tumor injection: A new enzyme-targeting radiosensitization treatment, Kochi Oxydol-Radiation Therapy for Unresectable Carcinomas, Type II (KORTUC II)", International J. Oncology, vol. 34, p. 609-618 (Nov. 27, 2008).
Shiho Tokuhiro et al., "Development of a novel enzyme-targeting radiosensitizer (KORTUC) containing hydrogen peroxide for intratumoral injection for patients with low linear energy transfer-radioresistant neoplasms", Oncology Letters, vol. I, p. 1025-1028 (2010).
Yasuhiro Ogawa et al., "Safety and effectiveness of a new enzyme-targeting radiosensitization treatment (KORTUC II) for intratumoral injection for low-LET radioresistant tumors", International J. Oncology, vol. 39, p. 553-560 (2011).
Wako BioWindow, MedGel, No. 111, p. 19 (2011).
Haller et al., "Oxygen embolism after hydrogen peroxide irrigation of a vulvar abscess", British J. Anaesthesia, vol. 88, No. 4, pp. 597-599 (2002).
Clinical Trial Results, "When Combined with Chemotherapy, Bevacizumab is Associated with Increased Risk of Death", Adapted from NCI Cancer Research Bulletin (Mar. 30, 2011).
Hall et al., Radiobiology for the Radiologist, 6th Edition, Chapter 25, "Radiosensitizers and Bioreductive Drugs", pp. 419-431 (2006).
Ogawa et al., Int. J. Radiation Oncology Biol. Phys., vol. 80, No. 1, pp. 111-118 (2011).
Mukai et al., "Final Results of a Safety and Efficacy Trial of Preoperative Sequential Chemoradiation Therapy for the Nonsurgical Treatment of Early Breast Cancer: Japan Clinical Oncology Group Study JCOG0306", Oncology, vol. 85, p. 336-341 (2013).
Ogawa et al., 20th Annual Meeting on the Sensitization of Cancer Treatment, Kochi Prefectural Culture Hall (Jun. 7, 2014).
Chinese Office Action with English translation dated Jan. 14, 2011 in corresponding Chinese Application No. 200780043347.2.
Supplementary European Search Report dated Feb. 28, 2011 in corresponding European Application No. 07807718.7.

* cited by examiner

RADIATION SENSITIZER OR ANTI-CANCER CHEMOTHERAPY SENSITIZER

TECHNICAL FIELD

This invention relates to a radiosensitizer or anti-cancer chemotherapy sensitizer, particularly to a radiosensitizer or anti-cancer chemotherapy sensitizer (injection composition for radiosensitizer or chemotherapy sensitizer application) applied to or injected into a tumor area prior to irradiation or anti-cancer chemotherapy (administration of anti-cancer agent). It also relates to anti-cancer therapy using the radiosensitizer or anti-cancer chemotherapy sensitizer of the invention.

BACKGROUND ART

Radiotherapy is second to surgical operations as a method of locally treating malignant tumors. Because it can be applied to elderly patients and also enables normal organs and tissues to be conserved, the number of patients being treated by the method is recently increasing very rapidly. However, linear accelerator-generated high-energy X-rays and electron beams that are generally used for the radiotherapy are low linear energy transfer (LET) radiation having a relatively low biological effect. Accordingly, linear accelerator based radiotherapy has little effect on tumors such as malignant melanoma, various types of sarcoma and glioblastoma multiforme and the like. Also, because locally advanced neoplasms that have grown to several centimeters or more have many hypoxic cancer cells or contain large amounts of anti-oxidative enzyme, and are therefore resistant to radiation, linear accelerator based radiotherapy has little effect.

Heavy particle beam therapy is a method used to improve the radiotherapeutic effect on these. However, the widespread use of heavy particle beam therapy is made difficult due to the large cost of the equipment, which involves an investment of several tens of billions of yen.

Since before, various radiosensitizers (such as, for example, Metronidazole, Misonidazole, Etanidazole, Nimorazole, and so forth) have been developed to increase the radiotherapeutic effect (see non-patent documents 1 to 3, for example). However, in addition to the uncertainty of their effect, they have side effects such as peripheral neuropathy and the like, and therefore are not yet allowed to be used in clinical practice.

Using radioresistant osteosarcoma cell lines (HS-Os-1), the present inventors previously confirmed that sensitivity to the radiation effect could be increased and apoptosis readily induced by adding a low concentration of hydrogen peroxide to a culture solution during the irradiation. Normally, such radioresistant osteosarcoma cells or chondrocytes suffer little DNA oxidative damage even when exposed to radiation of 30 Gy. In contrast, when irradiated in the presence of a low concentration (0.1 mM, for example) of hydrogen peroxide, reactive oxygen species can be clearly produced in cells exposed to radiation in the order of 10 Gy, giving rise to apoptosis. One cause that can be cited for the radiation resistance of osteosarcoma cells is the presence of anti-oxidative enzyme (peroxidase, catalase) in the cells. Hydrogen peroxide is thought to block the action of the anti-oxidative enzyme. That is, when irradiation is conducted in the presence of hydrogen peroxide, the action of the anti-oxidative enzyme is blocked and oxygen is produced, oxidizing the radioresistant hypoxic cells, thereby converting them to being highly sensitive to radiation (see, for example, non-patent documents 4 to 6).

Non-patent document 1: Chapman J D, Whitmore G F (eds): Chemical modifiers of cancer treatment. Int J Radiat Oncol Biol Phys 10: 1161-1813, 1984.

Non-patent document 2: Coleman C N.: Hypoxic cell radiosensitizers: Expectations and progress in drug development. Int J Radiat Oncol Biol Phys 11: 323-329, 1985.

Non-patent document 3: Radiobiology for the Radiologist (Sixth Edition) by Eric J. Hall and Amato J. Giaccia, Lippincott Williams & Wilkins, 419-431, 2006.

Non-patent document 4: Yasuhiro Ogawa et al.: Mechanism of apoptotic resistance of human osteosarcoma cell line, HS-Os-1, against irradiation. International Journal of Molecular Medicine 12: 453-458, 2003.

Non-patent document 5: Yasuhiro Ogawa et al.: Apoptotic-resistance of human osteosarcoma cell line HS-Os-1 to irradiation is converted to apoptotic-susceptibility by hydrogen peroxide: A potent role of hydrogen peroxide as a new radiosensitizer. International Journal of Molecular Medicine 12: 845-850, 2003.

Non-patent document 6: Yasuhiro Ogawa et al.: Immunocytochemical characteristics of human osteosarcoma cell line HS-Os-1: Possible implication in apoptotic resistance against irradiation. International Journal of Molecular Medicine 14: 397-403, 2004.

DISCLOSURE OF THE INVENTION

Based on the finding that hydrogen peroxide has the radiosensitization effect on osteosarcoma cell line as described above, the present inventor used sterilized cut cotton soaked in a hydrogen peroxide solution having a concentration of approximately 3 weight percent as a bolus for a case of inoperable locally advanced malignant melanoma (superficially-exposed carcinoma) which was then subjected to irradiation by an electron beam from a linear accelerator. Radiation was conducted three times a week, with each radiation dose amounting to 4 Gy, for a total radiation dose of 48 Gy, resulting in the good effect of the disappearance of the tumor (Reference Example 1).

However, hydrogen peroxide solution (or the hydrogen peroxide diluted with distilled water) is a strong irritant that should not be applied directly in a large quantity to an affected part, and further, its use is contraindicated where there is a risk that the hydrogen peroxide solution could seep into a body cavity such as in the case of a fistula or contused wound. Also, hydrogen peroxide is unstable, and when applied to the affected part immediately starts releasing oxygen, so that if it were to be injected as is subcutaneously or into human tissue, such as a tumor, there is a danger that it will be rapidly degraded into water and oxygen by the action of anti-oxidative enzymes, such as peroxidase and catalase, and cause complications such as pulmonary embolism. For that reason, there is a need for a pharmaceutical invention that can alleviate the irritation of hydrogen peroxide so that it can be applied to fistula or contused wounds or the like, or safely injected into the human body, and that also delays and suppresses the degradation of the hydrogen peroxide.

An object of the present invention is to provide a radiosensitizer or anti-cancer chemotherapy sensitizer that is devised to enable the radiosensitizer and anti-cancer chemotherapy sensitizer effect to be efficiently exerted by relieving the irritation that hydrogen peroxide has on an affected area, can be safely injected into the human body, and can delay or reduce the degradation of the hydrogen peroxide.

Means for Solving the Problems

Through diligent study aimed at solving the above problems, it was found that the irritation of hydrogen peroxide on the skin as well as the irritation with respect to mucous membranes and tissues could be reduced by combining hyaluronic acid or a salt thereof with the hydrogen peroxide. Moreover, it was found that by combining hyaluronic acid or a salt thereof with the hydrogen peroxide, the tendency of the hydrogen peroxide to readily give off oxygen due to its instability can be reduced, and even when it is injected into the human body, the rapid degradation of the hydrogen peroxide due to the action of anti-oxidative enzymes is significantly reduced, enabling the radiation sensitizing effect and anti-cancer chemotherapy sensitizing effect to be exerted more safely and efficiently.

The present invention was accomplished based on the above findings, and is characterized by having the following composition.

(I) Radiosensitizer or Anti-Cancer Chemotherapy Sensitizer (I-1) A radiosensitizer or anti-cancer chemotherapy sensitizer comprising a combination of (a) hydrogen peroxide and (b) hyaluronic acid or a salt thereof.

(I-2) A radiosensitizer or anti-cancer chemotherapy sensitizer described in (I-1) that is in a form of a combination preparation of (a) component and (b) component mixed beforehand.

(I-3) A radiosensitizer or anti-cancer chemotherapy sensitizer described in (I-1) that is used in a form in which (a) component and (b) component are mixed at time of use. Said form includes a kit having at least (a) a formulation containing hydrogen peroxide and (b) a formulation containing hyaluronic acid or a salt thereof.

(I-4) A radiosensitizer or anti-cancer chemotherapy sensitizer described in any of (I-1) to (I-3) that has the form of an injection or may be used as an injection.

(I-5) A radiosensitizer or anti-cancer chemotherapy sensitizer described in any of (I-1) to (I-4) in which the hydrogen peroxide content in the final formulation is 0.01 to 3.5 weight percent.

(I-6) A radiosensitizer or anti-cancer chemotherapy sensitizer described in any of (I-1) to (I-5) in which the content of the hyaluronic acid or a salt thereof in the final formulation is 0.1 to 10 weight percent.

(I-7) A radiosensitizer or anti-cancer chemotherapy sensitizer described in any of (I-1) to (I-6) that may be used by intratumoral injection into the area that is resistant to radiotherapy or resistant to anti-cancer chemotherapy.

(I-8) A radiosensitizer or anti-cancer chemotherapy sensitizer described in any of (I-1) to (I-7) that is used on a tumor area prior to irradiation or anti-cancer chemotherapy in a case of radiotherapy of a radioresistant tumor or anti-cancer chemotherapy of an anti-cancer chemotherapy resistant tumor.

(I-9) A radiosensitizer described in (I-8) in which the irradiation is performed using an X-ray beam or electron beam from a linear accelerator.

(II) Radiotherapy Sensitizing Method or Anti-Cancer Chemotherapy Sensitizing Method.

(II-1) A radiotherapy or anti-cancer chemotherapy sensitizing method having a step of processing of a tumor area by the radiosensitizer or anti-cancer chemotherapy sensitizer described in any of (I-1) to (I-6), at the same time as or prior to irradiation or anti-cancer chemotherapy in the course of radiotherapy or anti-cancer chemotherapy of a tumor.

(II-2) The sensitizing method described in (II-1) in which the tumor is a tumor that is resistant to radiotherapy or resistant to anti-cancer chemotherapy.

(II-3) The sensitizing method described in (II-1) or (II-2) in which the processing is an intratumoral injection of the radiosensitizer or anti-cancer chemotherapy sensitizer described in any of (I-1) to (I-6).

(II-4) The sensitizing method described in any of (II-1) to (II-3) in which the irradiation is performed using an X-ray beam or electron beam from a linear accelerator.

(II-5) A sensitizing method described in any of (II-1) to (II-3) in which the anti-cancer chemotherapy is an administration of an anti-cancer agent to a patient.

(III) Radiosensitization Method or Anti-Cancer Chemotherapy Sensitization Method (III-1) a Radiosensitization Method or Anti-Cancer Chemotherapy Sensitization Method Comprising (1) a step of processing a tumor area with the radiosensitizer or anti-cancer chemotherapy sensitizer of any of (I-1) to (I-6), and (2) a step of exposing the processed tumor area to irradiation or the patient to anti-cancer chemotherapy.

(III-2) A radiosensitization method or anti-cancer chemotherapy sensitization method described in (III-1) in which the tumor is a tumor that is resistant to radiotherapy or resistant to anti-cancer chemotherapy.

(III-3) A radiosensitization method or anti-cancer chemotherapy sensitization method described in (III-1) or (III-2) in which the processing is an intratumoral injection of the radiosensitizer or anti-cancer chemotherapy sensitizer described in any of (I-1) to (I-6).

(III-4) A radiosensitization method or anti-cancer chemotherapy sensitization method described in any of (III-1) to (III-3) in which the irradiation is irradiation by an X-ray beam or electron beam produced by a linear accelerator.

(III-5) A radiosensitization method or anti-cancer chemotherapy sensitization method described in any of (III-1) to (III-3) in which the anti-cancer chemotherapy is an administration of an anti-cancer agent to the patient.

(IV) Use for Sensitizing Radiotherapy or Sensitizing Anti-Cancer Chemotherapy (IV-1) Use of a radiosensitizer or anti-cancer chemotherapy sensitizer described in any of (I-1) to (I-6) for sensitizing radiotherapy or for sensitizing anti-cancer chemotherapy.

(V) Method of Alleviating Pain of Radiosensitizer or Anti-Cancer Chemotherapy Sensitizer (V-1) A method of alleviating pain of the radiosensitizer or anti-cancer chemotherapy sensitizer in the tumor area characterized by combining (a) hydrogen peroxide and (b) hyaluronic acid or a salt thereof.

Effect of the Invention

In accordance with the radiosensitizer and radiosensitization method using the same of this invention, it is possible to obtain a superior radiotherapeutic effect using low-LET beams, even with respect to radioresistant tumors because they contain many hypoxic cells.

Also, the anti-cancer chemotherapy sensitizer of the invention increases the effect of the anti-cancer chemotherapy (anti-cancer drug treatment) by inactivating anti-oxidative enzymes in the tumor region. Thus, in accordance with the anti-cancer chemotherapy sensitization method of this invention in which the anti-cancer chemotherapy sensitizer of the invention is combined with anti-cancer chemotherapy, it is possible to obtain a superior anti-cancer treatment effect even with cancers that are intractable to anti-cancer chemotherapy.

BEST MODE FOR CARRYING OUT THE INVENTION

The radiosensitizer or anti-cancer chemotherapy sensitizer of the present invention is characterized by comprising a combination of (a) hydrogen peroxide and (b) hyaluronic acid or a salt thereof.

The radiation and anti-cancer chemotherapy sensitizer according to the invention is a pharmaceutical compound that can be used on a tumor area prior to, or simultaneously with, radiotherapy (irradiation) as well as anti-cancer chemotherapy, to strengthen the effect that radiotherapy and anti-cancer chemotherapy has on the tumor area.

In this invention, "anti-cancer chemotherapy" means all treatments based on anti-cancer agents (carcinostatic agents). Linear accelerator based radiotherapy of cancer cells has around a 70% dependency on the production of reactive oxygen species such as hydroxyl radicals. The mechanisms of various anti-cancer agents (carcinostatic agents) have this point in common. Therefore, a substance that increases the sensitivity of the radiotherapy effect at the same time increases the sensitivity of the anti-cancer chemotherapy effect.

The hyaluronic acid used by the invention may be derived from any source; it may be extracted from animal tissues or manufactured by a fermentation method. For safety and manufacturing stability, it is preferably manufactured by a fermentation method. There is no particular limitation on the strain used in the fermentation method, any hyaluronic acid producing microorganism desired being usable, such as, for example, a hyaluronic acid producing organism isolated from nature that belongs to a genus such as *Streptococcus*, the *Streptococcus* equi FM-100 described in JP63-123392A (Fermentation Research Institute *Bacillus* Deposit No. 9027) or the *Streptococcus* equi FM-300 described in JP2-234689A (Fermentation Research Institute *Bacillus* Deposit No. 2319).

Heretofore, hyaluronic acids having various molecular weights have been known. While it is not a limitation, the present invention can use hyaluronic acid having a molecular weight normally about 500000 to about 10 million, preferably about 500000 to about 8 million, and more preferably about 500000 to about 5 million.

The weight average molecular weight of the hyaluronic acid can be measured by the SEC-MALLS method comprising using a size-exclusion chromatogram (SEC) coupled to a multi-angle laser light-scattering detector (MALLS) (see, for example, C. Yomota, Bull. Natl. Inst. Health Sci., 121, 030-033 (2003)).

The hyaluronic acid that is an object of the invention may be crosslinked hyaluronic acid. Here, crosslinked hyaluronic acid is a macro-molecule having a three-dimensional mesh structure that forms a gel that swells in the medium. That is, crosslinked hyaluronic acid has a hydrogel morphology that swells in a physiologically permissible medium.

As an example of a crosslinked hyaluronic acid, there can be mentioned a crosslinked hyaluronic acid formed from a hyaluronic acid having a weight average primary molecular weight that is greater than 800000. The crosslinked hyaluronic acid is characterized in that, when it is severed at the crosslink point, it forms a straight-chain hyaluronic acid having a weight average molecular weight that is greater than 800000. The degree of branching and the weight average molecular weight of the hyaluronic acid produced by cutting at the crosslink point can be readily measured by GPC-MALLS (multi-angle light scattering) using a multi-angle laser light-scattering detector (MALLS) and a differential refractive index detector with a gel permission chromatogram (GPC).

The crosslinked hyaluronic acid used by the invention may be one in which the crosslink point is hydrolyzable. Here, a crosslink point that is hydrolyzable means one wherein, under physiological conditions such as at 37° C. and a pH of 7.4, in a physiological saline solution, the crosslink point is apt to degrade before the main chain of the hyaluronic acid. While crosslink structures having a hydrolyzability that is superior to the main chain degradation of the hyaluronic acid that can be cited include carbamate bonds, hydrozone bonds, hydrazide bonds, phosphate and ester bonds, the most typical structures are ester bonds.

Examples of crosslinked hyaluronic acids having an ester bond crosslinked structure include esters of carboxyl group of hyaluronic acid and polyhydric alcohol, esters of hydroxyl group of hyaluronic acid and polyhydric carboxylic acid, esters of carboxyl group of hyaluronic acid and polyhydric epoxide, and so forth. The crosslinked hyaluronic acid concerned includes a crosslinked hyaluronic acid in which there is a direct ester bond between the carboxyl group and the hydroxyl group of the hyaluronic acid (called a bridge ester having a self-crosslinked ester bond, or a hyaluronic acid having a self-crosslinked ester bond).

A hyaluronic acid having self-crosslinked ester bonds can be manufactured by methods that are public knowledge. For example, as described in EP 0341745 B1, a hyaluronic acid having self-crosslinked ester bonds can be manufactured by esterifying a part or all of the carboxyl groups with the alcoholic functions of the same polysaccharide chain or other polysaccharide chains; or by the method described by WO 99/10385 in which a solution of a hyaluronic acid is acidified, and the solution is frozen and thawed at least once to thereby prepare a hyaluronic acid having self-crosslinked ester bonds; or by the method described in WO 01/57093, in which without freezing, a hyaluronic acid and an acidic solution are mixed together to produce a 5% or higher concentration and the state of coexistence is maintained to thereby prepare a hyaluronic acid having self-crosslinked ester bonds.

Because the natural hyaluronic acid emitted by hydrolysis of the hyaluronic acid having self-crosslinked ester bonds is metabolized by physiological metabolic pathways, it is considered to be safer than a crosslinked hyaluronic acid manufactured by other crosslinking reactions.

As a crosslinked hyaluronic acid, there can be mentioned a hyaluronic acid in which the carboxyl group of the hyaluronic acid is crosslinked to the hydroxyl group of the same hyaluronic acid molecules, and/or to the hydroxyl group of different hyaluronic acid molecules (see, for example, JP 2003-252905 A).

The degree of crosslinking of a crosslinked hyaluronic acid, for example, the amount of intermolecular ester bonding of the molecules to be introduced, can be arbitrarily controlled according to the purpose of the crosslinked hyaluronic acid or the required properties thereof. The amount of ester bonding can be defined as the ratio to the total number of carboxyl groups in the hyaluronic acid. In the radiosensitizer or anti-cancer chemotherapy sensitizer of this invention, the hyaluronic acid is preferably used as a water solution or a water swelling gel. When the hyaluronic acid is used in the form of a water solution, while there is no limitation, it is preferable to use a crosslinked hyaluronic acid in which the amount of intermolecular ester bonding is less than 0.5%. Also, when the hyaluronic acid is used as a water swelling gel, while there is no limitation, it is preferable to use a crosslinked hyaluronic acid in which the amount of intermolecular ester bonding is about 0.5% to about 1%. The molecular structure of the crosslinked hyaluronic acid can be confirmed by using NMR (Carbohydr. Res. Vol 245, p 113-128, 1993; Macromolecules Vol 29, p 2894-2902, 1996).

A crosslinked hyaluronic acid can be prepared by, for example, acidifying a water solution of hyaluronic acid and converting the dissociated carboxyl groups to the acid form. Because under high-temperature conditions an N-acetyl-D-glucosamine unit deacetylation reaction is produced that competes with the crosslinking reaction, it is desirable to reduce the reaction temperature of the process used to acidify the hyaluronic acid water solution (see JP H1-266102 (A)). The reaction temperature used to give precedence to crosslink formation is preferably not higher than room temperature, and is more preferably not more than 10° C. Also, to promote the intermolecular esterification reaction, it is preferable to raise a hyaluronic acid concentration. For example, the hyaluronic acid concentration of the reaction solution is preferably 5 weight percent or above, and more preferably 10 weight percent or above. Also, the intermolecular esterification reaction can be promoted by adding to the reaction system a substance that catalyzes the dehydration-condensation reaction. An acidic catalyst is commonly used as a catalyst for promoting the dehydration-condensation reaction, for which sulfuric acid, hydrochloric acid or a sulfonic acid derivative of an aromatic compound or the like may be used.

When the crosslinked hyaluronic acid is being formed, it may be mixed or compounded with materials having the same good biocompatibility as the hyaluronic acid, for example, chondroitin sulfate, carboxymethyl-cellulose, and so forth. It is also possible to add pharmacologically or physiologically active substances to form a crosslinked hyaluronic acid containing such substances.

The crosslinked hyaluronic acid thus obtained can next be subjected to an operation to adjust the acidity by removing acid components. This removal of acid components is normally performed in a water solvent by, for example, washing or dialyzing. There is no particular limitation on the water solvent that may be used, provided it does not impair the function of the crosslinked hyaluronic acid. Examples of the usable water solvents include water, physiological saline, a phosphoric acid buffer solution and so forth, but it is preferable to use physiological saline or a phosphoric acid buffer solution and the like. When acid form carboxyl groups remain after the crosslinked hyaluronic acid has been washed, they can be formed into a salt of sodium or the like (salification). There is no particular limitation on the salification method used, and applicable methods include, for example, using a water solution of sodium hydroxide to adjust the crosslinked hyaluronic acid solution to a pH of around 7, or immersing the crosslinked hyaluronic acid in physiological saline or a phosphoric acid buffer physiological saline solution.

Depending on the purpose, the crosslinked hyaluronic acid thus prepared may be used in solution form, in the solvent immersion state, or in a moist state that includes the solvent, as the material of the radiosensitizer or anti-cancer chemotherapy sensitizer of the invention (hereinafter also referred to simply as "the sensitizer").

The crosslinked hyaluronic acid swells to a gel in a physiologically permissible medium. Therefore, when the sensitizer of the invention is used as an injection, in order to inject it through a needle into the area of the tumor to be subjected to irradiation or anti-cancer chemotherapy, it is necessary for the crosslinked hyaluronic acid (gel) to be dispersed as a suspension in a physiologically permissible medium. The suspension may be prepared by crushing the crosslinked hyaluronic acid at either the manufacturing or refining process stage thereof, using a crusher such as a mixer or homogenizer. The diameter of the hydrogel particles may be arbitrarily adjusted. However, after the crosslinked hyaluronic acid has been dispersed in the physiologically permissible medium and homogenized, the dispersion particle diameter can be readily adjusted normally from about 0.05 to about 2 μm.

The equilibrium swelling ratio of the crosslinked hyaluronic acid gel can be adjusted arbitrarily according to the degree of crosslinking of the crosslinked hyaluronic acid. For example, in the case of an equilibrium swelling ratio of 100 times, the concentration of the hyaluronic acid in the physiologically permissible medium will be 1%. In the case of an equilibrium swelling ratio of 10 times, the concentration of the hyaluronic acid in the physiologically permissible medium will be 10%.

In the sensitizer of this invention, as mentioned in the foregoing, an ordinary hyaluronic acid (non-crosslinked), a crosslinked hyaluronic acid, or an arbitrary combination thereof may be used. A hyaluronic acid in a single form or a hyaluronic acid of a single molecular weight may also be used. Further, various crosslinked hyaluronic acids or hyaluronic acids of various molecular weights may be used in combination.

In the sensitizer of this invention, a hyaluronic acid (as a general concept that includes a crosslinked hyaluronic acid) may be used in the form of a salt. Suitable examples of hyaluronic acid salts are, but are not limited to, alkali metal salts such as sodium, potassium, lithium, and so forth. A sodium salt of hyaluronic acid is preferable.

The proportion of hyaluronic acid or a salt thereof contained in the sensitizer of the invention (the final formulation) is not limited, and may be selected from the range of 0.1 to 10 weight percent. 0.1 to 5 weight percent is preferable, and 0.1 to 3 weight percent is more preferable.

According to the sensitizer of the invention, at least one member selected from the group consisting of liposomes, polymer gels and gelatins may be used in place of the above hyaluronic acid or a salt thereof, or in combination therewith.

Here, a liposome refers to a multilayer capsule structure formed of a phospholipid. Preferably, the liposome is hollow. Using the liposome enables the radiosensitizer or anti-cancer chemotherapy sensitizer to be prepared as a liposome formulation in which a hydrogen peroxide solution is encapsulated by the membrane of a phospholipid microparticle or within a phospholipid microparticle. Such a liposome formulation can be readily prepared by adding a hydrogen peroxide solution into the hollow liposome (at a temperature of, for example, about 16 to about 40° C.), and then softly stirring by rotating the resulting product by hand 3 to 5 times. Liposomes are commercially available, examples being the EVTRASOME (trademark) series (NOF Corporation) and the Cortosome EL series (Funakoshi Corporation).

The proportion of liposomes contained in the sensitizer of the invention (the final formulation) is not limited, and may be suitably selected from the range of 0.01 to 10 weight percent.

For a polymer gel, the polymer gels disclosed in the publication of Haaga et al. (Combined tumor therapy by using radiofrequency ablation and 5-FU-laden polymer implants: evaluation in rats and rabbits. Radiology 237: 911-918, 2005) may be used.

The proportion of polymer gel contained in the sensitizer of the invention (the final formulation) is not limited, and may be suitably selected from the range of 0.01 to 10 weight percent.

With respect to gelatin, there is no particular limitation as long as it is one that can be applied to the human body such as for medical or cosmetic use or for edible use. A gelatin for medical application defined by a pharmacopeia is preferable. Such gelatins are widely available commercially, for example, a porous gelatin (trade name: "Gelpart," Astellas Pharma Inc.) sold as an intravascular emboli-promoting prosthetic material.

The proportion of gelatin contained in the sensitizer of the invention (the final formulation) is not limited, and may be suitably selected from the range of 0.01 to 5 weight percent.

The sensitizer of the invention is characterized by comprising a combination of at least one of the aforementioned components (also referred to in the invention as "(b) component") and hydrogen peroxide (also referred to in the invention as "(a) component"). Preferably, the combination is of a hyaluronic acid or a salt thereof ((b) component) and hydrogen peroxide ((a) component).

Here, "a combination" is used to inclusively mean the sensitizer of the invention that is used (i) in a state in which both the (a) component and the (b) component are included from the beginning (combination preparation);

(ii) for sale as a combination (a kit) including a separately packaged formulation containing the (a) component and a separately packaged formulation containing the (b) component; or (iii) in a formulation containing the (a) component and a formulation containing the (b) component that are separately packaged and are in separate market distribution channels and are combined at time of use.

That is, in this invention, "radiosensitizer or anti-cancer chemotherapy sensitizer comprising a combination" means that the radiosensitizer or anti-cancer chemotherapy sensitizer that is ultimately used (referred to in this invention as the "final formulation") may include both the (a) component and the (b) component, with the form at the sales and distribution stage being immaterial.

The proportion of the hydrogen peroxide used as the (a) component in the final formulation of the radiosensitizer or anti-cancer chemotherapy sensitizer of the invention is not limited, and may be suitably selected from the range of 0.01 to 3.5 weight percent. It is preferably 0.05 to 3 weight percent, and more preferably 0.1 to 2 weight percent.

The composition ratio of the hyaluronic acid or a salt thereof to the hydrogen peroxide is not limited. The total amount of the hyaluronic acid or a salt thereof may be suitably selected from the range of 1 to 10000 parts by weight per 100 parts by weight of hydrogen peroxide, preferably 10 to 1000 parts by weight, and more preferably 50 to 150 parts by weight.

There is also no limitation on the composition ratio of the liposomes, polymer gel or gelatin to the hydrogen peroxide, which may be adjusted in accordance with the above-described examples of hyaluronic acid or salts thereof. For example, the amount of liposomes may be suitably selected from the range of 1 to 10000 parts by weight per 100 parts by weight of hydrogen peroxide, preferably 10 to 1000 parts by weight, and more preferably 50 to 150 parts by weight. The amount of gelatin may be suitably selected from the range of 1 to 10000 parts by weight per 100 parts by weight of hydrogen peroxide, preferably 10 to 1000 parts by weight, and more preferably 50 to 500 parts by weight.

In addition to the above (a) component and (b) component, the sensitizer of the invention may include medically permissible physiological saline, a phosphoric acid buffer solution (for example, sodium chloride, sodium dihydrogen phosphate, and sodium dihydrogen phosphate, and the like). While there is no limitation on the humoral property of the sensitizer of the invention, provided it is compatible with the human body, it is preferable to adjust the pH to a range of 6 to 8.5, and more preferably to a range of 6.8 to 7.8.

The sensitizer of the invention is a liquid (including a solution, emulsion or suspension) or a gel, other than which there are no particular limitations on how it is used (the usage). For example, when the sensitizer liquid or gel is an external preparation for use during irradiation, prior to the irradiation, the sensitizer liquid or gel can be applied by methods such as spraying or coating it directly onto the tumor area or adhering it thereto, or impregnating sterile cotton or gauze with the sensitizer for application to the tumor area to be irradiated during the irradiation.

When the sensitizer liquid or gel of the invention is an injection form, the injection can be directly intratumorally injected using a syringe or the like or indirectly injected via an angiography catheter into the tumor area at time of the irradiation. In this case, the sensitizer liquid or gel of the invention can be injected into the target tumor area using a syringe or angiography catheter, before, after or at the same time as the administration of the anti-cancer agent. Specifically, it is preferable to use a syringe having a needle of about 21 gauge to perform the intratumoral injection guided by ultrasonographic examination while observing the state of permeation of the sensitizer into the tissue. The sensitizer can be delivered widely to the tissue under ultrasonographic guidance to modify the depth and direction of the injection needle. The dose of sensitizer administered to the tumor area will differ depending on the size of the tumor and the administration method. When, for example, it is intratumorally injected, the dose (injection amount) is normally about 1 to about 5 ml, and preferably about 3 ml.

Preferably, the radiosensitizer or anti-cancer chemotherapy sensitizer of the invention is in the form of an injection (a radiosensitizer injection or anti-cancer chemotherapy sensitizer injection). The injection can be obtained by preparing an aqueous solution using water for injection (distilled water for injection, sterile water for injection, etc.), an isotonizing agent, a pH adjustment, and a buffer solution and the like. The (a) component and the (b) component are added to the resulting aqueous solution in the proportions of the above-described range. The resulting mixture is placed in a container and the container is then sealed, followed by sterilization using a high-pressure steam sterilization, autoclave sterilization or the like. It is also possible to prepare a sensitizer of the invention by suitably mixing a formulation containing the (a) component and a formulation containing the (b) component at time of use (a preparation of type prepared just before use), using water for injection (distilled water for injection, sterile water for injection, etc.), if required.

Examples of usable isotonizing agents include sodium chloride, glycerin, glucose, polyethylene glycol, propylene glycol, D-mannitol, fructose, xylitol, sodium dihydrogen phosphate and sodium phosphate. Preferably, sodium chloride is used. As the pH adjustment, there may be used hydrochloric acid or sodium hydroxide or the like. The pH is adjusted as described above to a range of 6 to 8.5, and preferably to a range of 6.8 to 7.8. Examples of the buffer solutions that can be used for maintaining the pH include phosphoric acid buffer solutions, tris buffer solutions and acetic acid buffer solutions. Preferably, a phosphoric acid buffer solution is used.

As described in the above, in radiotherapy, the radiosensitizer of the invention is used on a tumor area prior to irradiation. It can be preferably used in radiotherapy of tumors that are radioresistant.

Examples of tumors that are radioresistant include tumors that have many hypoxic tumor cells and tumors that have a lot of anti-oxidative enzyme. The biggest problem with cancer radiotherapy, which currently is conducted mainly with linear accelerators, is the presence of radioresistant cancer cells. The radioresistant tumor tissues are mostly in hypoxic regions and exhibit resistance to radiotherapy. In a hypoxic state, the radiation-resistance of these cells' DNA damage induced by the radiation is not fixed by oxygen. Moreover, reactive oxygen species produced in the cancer cells by the radiation are eliminated by anti-oxidative enzymes, which is said to make it difficult to induce apoptosis. Specific examples of tumors that are radioresistant include malignant melanomas, malignant glioblastomas and various types of sarcomas such as osteosarcomas, as well as nearly all types of locally advanced neoplasms that have grown to several centimeters or more.

Radiotherapy using the radiosensitizer of the invention can be implemented by first applying the radiosensitizer to the area of the tumor to be irradiated, and then preferably using a linear accelerator to irradiate the affected part with X-rays or an electron beam. While the X-ray conditions will differ depending on how far the tumor has advanced and its size and the like, a normal dose will be 1.5 to 3 Gy, preferably around 2 Gy, 2 to 5 times a week, and preferably 4 or 5 times a week, over a period of 1 to 5 weeks, for a total dose of 20 to 70 Gy, preferably 40 to 70 Gy, and more preferably 50 to 60 Gy. While the electron beam conditions will also differ depending on how far the tumor has advanced and its size and the like, a normal dose will be 2 to 5 Gy, preferably around 4 Gy, 1 to 5 times a week, and preferably 2 or 3 times a week, over a period of 1 to 5 weeks, for a total dose of 30 to 70 Gy, and preferably 40 to 60 Gy.

The anti-cancer chemotherapy sensitizer of the invention may be used on the tumor area to be treated (preferably by injection), prior to anti-cancer chemotherapy (administration of anti-cancer agent). Preferably, it can be used on tumors that are difficult to treat with anti-cancer chemotherapy or which are relatively large. Many solid tumors exhibit resistance to anti-cancer chemotherapy, such as stomach cancer, non-small-cell lung cancer, colorectal and rectal cancer, liver cancer, pancreatic cancer, uterine cancer and cancer of the esophagus. Nearly all locally advanced solid tumors are resistant to anti-cancer chemotherapy.

Anti-cancer chemotherapy using the anti-cancer chemotherapy sensitizer of the invention can be implemented in parallel with the administration of anti-cancer agents (before, after or at the same time as the administration of the anti-cancer agents), by applying the anti-cancer chemotherapy sensitizer of the invention to the target tumor area. As described above, the sensitizer is intratumorally injected preferably using a needle or a catheter guided by ultrasonographic examination. While the chemotherapy sensitizer injection conditions may differ depending on how far the tumor has advanced and its size and the like, a method may be used in which normally each injection is from 1 ml to 5 ml, preferably 3 ml, administered 1 to 5 times a month, preferably 1 or 2 times every other week.

EXAMPLES

The invention will now be described in detail with reference to Examples and Formulation Examples. However, the invention is not limited to these examples. In the following, also, unless otherwise specified the amounts of the components are expressed in weight percent. All of the treatments described in the following examples were conducted with the approval of the ethics committee of Kochi Medical School and based on the wishes of the patients.

Formulation Example 1

To 1 syringe (2.5 ml) of a hyaluronic acid preparation having a 1% concentration of sodium hyaluronate [(trade name: "ARTZ Dispo," made by Seikagaku Corporation); 1 syringe (2.5 ml) of the preparation contains 25 mg of sodium hyaluronate, 2.5 mg of L-methionine, sodium chloride, sodium hydrogenphosphate, crystalline sodium dihydrogen phosphate, and an isotonizing agent. The preparation is colorless, transparent viscous aqueous solution having a pH of 6.8 to 7.8, specific osmotic pressure of 1.0 to 1.2 (relative to physiological saline) and a weight average molecular weight of 600000 to 1.2 million], 0.5 ml of a 3% solution of hydrogen peroxide was added immediately before use, and mixed well to prepare the radiosensitizer or anti-cancer chemotherapy sensitizer of the invention. These sensitizers have a sodium hyaluronate concentration of 0.83% and a hydrogen peroxide concentration of approximately 0.5%. This preparation was used in the following examples.

Formulation Examples 2 to 7

The concentrations of the sodium hyaluronate and hydrogen peroxide in the final formulations (Formulation Examples 2 to 7) of the radiosensitizer or anti-cancer chemotherapy sensitizer of the invention are shown in the following Table 1.

The radiosensitizer or anti-cancer chemotherapy sensitizer can be prepared using the hyaluronic acid preparation (trade name: "ARTZ Dispo," made by Seikagaku Corporation) and hydrogen peroxide used in Formulation Example 1.

TABLE 1

|  | Formulation Example 2 | Formulation Example 3 | Formulation Example 4 | Formulation Example 5 | Formulation Example 6 | Formulation Example 7 |
| --- | --- | --- | --- | --- | --- | --- |
| Sodium Hyaluronate | 0.96 | 0.89 | 0.71 | 0.55 | 0.50 | 0.33 |

TABLE 1-continued

|  | Formulation Example 2 | Formulation Example 3 | Formulation Example 4 | Formulation Example 5 | Formulation Example 6 | Formulation Example 7 |
|---|---|---|---|---|---|---|
| Hydrogen Peroxide | 0.12 | 0.36 | 0.86 | 1.33 | 1.50 | 2.00 |

Reference Example 1

For a case of inoperable locally advanced malignant melanoma, sterilized cut cotton soaked in a hydrogen peroxide solution having a concentration of approximately 3 weight percent was used as a bolus, and irradiation by an electron beam from a linear accelerator (radiosensitization therapy) was then conducted.

Specifically, sterilized cut cotton soaked in a hydrogen peroxide solution having a concentration of approximately 3% was applied to the affected area of the locally advanced malignant melanoma as a bolus, and irradiation was conducted three times a week for four weeks, with each radiation dose amounting to 4 Gy (12 times, for a total radiation dosage of 48 Gy). FIG. 1 shows the effect of the radiosensitization method using the hydrogen peroxide solution. As can be seen from the figure, the malignant melanoma, which was approximately 8 cm long before the radiotherapy (Pre-radiotherapy (RT)), had shrunk to a length of approximately 5 cm two weeks after termination of the radiotherapy (2 weeks after RT), and at three months after termination of the radiotherapy, the tumor had been almost disappeared (3 months after RT).

Example 1

(1) Mouse squamous epithelium cancer cells (SCCVII tumor cells) were transplanted into the right leg of the same kind of C3H/He mouse (8-week-old female), and the following experiment was conducted when the tumor had grown to about 10 mm in diameter.

When a 27-gage thin needle was used to intratumorally inject 1 ml of physiological saline (pH 6.8) containing 0.5% hydrogen peroxide into the tumors of five mice, the mice were all observed to feel strong pain, violently resisting the injection. On the other hand, when a 27-gage thin needle was used to intratumorally inject 1 ml of the sensitizer of Formulation Example 1 (pH 6.8) containing 0.5% hydrogen peroxide and 0.83% sodium hyaluronate into the tumors of other five other mice, it was observed that the pain of the injection was alleviated, with none of the mice becoming overly disturbed.

(2) Based on the above results, the following experiment was conducted on five normal volunteers.

When a 27-gage thin needle was used to subcutaneously inject 1 ml of physiological saline (pH 6.8) containing 0.5% hydrogen peroxide into the inside of the left arms of five normal volunteers, all complained of severe pain limited to the injection site that lasted about 1 hour. On the other hand, when a 27-gage thin needle was used to subcutaneously inject 1 ml of the sensitizer of Formulation Example 1 (pH 6.8) containing 0.5% hydrogen peroxide and 0.83% sodium hyaluronate into the inside of the right arms of five normal volunteers, all of the volunteers felt almost no pain at the injection site.

The results of the above experiments show that the irritation caused by hydrogen peroxide can be alleviated by the coadministration of hydrogen peroxide and hyaluronic acid.

Example 2

A radiosensitizer prepared by the method of Formulation Example 1 was applied to a case of a recurrent inoperable malignant fibrous histiocytoma (a large, 3 cm subcutaneous tumor on right femoral region), followed by electron beam irradiation by linear accelerator (radiosensitization therapy). In parallel, power doppler ultrasound was used to measure blood flow signals in the tumor and the radiotherapeutic effect was evaluated. The results are shown in FIG. 2.

The malignant fibrous histiocytoma was irradiated three times a week for two weeks, with each of the six doses being 4 Gy, for a total dosage of 24 Gy, at which point abundant blood flow was observed in the tumor, showing that the radiotherapy had little effect (Figure: Recurrent MFH 24 Gy). Then, 3 ml of radiosensitizer was intratumorally injected, followed by irradiation. When the irradiation was continued following intratumorally injecting the radiosensitizer, the tumor blood flow signals were observed to be considerably reduced (Figure: 36 Gy) at the time the total dosage reached 36 Gy. When another 3 ml of radiosensitizer was intratumorally injected followed by irradiation, there was a further reduction in the blood flow in the tumor (Figure: 48 Gy) at the end of 48 Gy of radiotherapy. One week after the termination of 48 Gy of radiotherapy, almost no blood flow signals could be observed (Figure: 1 week after 48 Gy), from which it was understood that the tumor had necrosed due to the radiosensitization method according to the invention.

Example 3

A radiosensitizer prepared by the method of Formulation Example 1 was applied to right axillary metastatic lymph nodes and to right supra- and infra-clavicular metastatic lymph nodes in a case of breast cancer that in addition to being inoperable was unaffected by anti-cancer chemotherapy, and X-ray irradiation by linear accelerator was performed (radiosensitization therapy). In parallel, computerized tomography (CT) images were obtained to evaluate the radiotherapeutic effect.

FIG. 3 on the left shows an image of the right side of the patient's chest, from the thorax to the neck region. FIG. 3 on the upper right is a coronal image of the part obtained by computerized tomography (CT). FIG. 3 on the lower right is a PET-CT frontal image of the patient. In the PET-CT image of FIG. 3 on the lower right, the reddened portions on the lower right side and at the base of the neck on the right are the foci (the brain is where the PET drug usually accumulates).

FIG. 4 on the upper left shows a CT image of the neck region prior to radiotherapy, and FIG. 4 on the lower left shows a CT image of the part below the right axilla prior to radiotherapy. A radiotherapy planner device (Pinnacle 3) was used to plan linear accelerator X-ray radiotherapy of the neck region and below the right axilla, and tangential non-opposed quadrilateral portal radiation was conducted at uniformly distributed doses of 2.75 Gy for a total irradiation of 48.5 Gy. The figures on the right side of FIG. 4 are CT images taken after 7 irradiations (total dose of 19.25 Gy). However, radiosensitization method using the radiosensitizer was conducted only for the right axilla, and not for the right neck portion. Specifically, irradiation was conducted after the intratumoral injection of 3 ml of radiosensitizer into the tumor of the right axilla (to implement 3 sensitized radiation therapies at a rate of twice a week). Irradiation of the right neck portion was conducted without injecting a radiosensitizer.

FIG. 4 on the upper right is a CT image of the right neck portion taken after irradiation of 19.25 Gy, and FIG. 4 on the lower left is a CT image of the right axilla after irradiation of 19.25 Gy. As can be seen in FIG. 4 on the upper right, no change can be seen in the size of the right cervical lymphadenopathy that has been irradiated without being injected with the radiosensitizer. On the other hand, with respect to the giant metastatic lymph nodes of the right axilla, the pre-radiation CT value of approximately 65 had decreased to approximately 24 when the irradiation amount reached 19.25 Gy. Also, from the image, it can be seen that necrosis has been induced (FIG. 4 on the lower right). These results show that a pronounced radiosensitization effect is obtained by using the radiosensitizer of the invention in combination with the radiotherapy.

Example 4

With respect to the implementation of the widely-used anti-cancer EC chemotherapy (four drip infusions of 100 mg/m$^2$ of Epirubicin administered in combination with 600 mg/m$^2$ of cyclophosphamide every three weeks (four courses)) on two patients suffering from locally advanced breast cancers that were intractable to anti-cancer chemotherapy, just prior (2 or 3 hours) to the anti-cancer chemotherapy (administration of anti-cancer agent), 3 ml of an anti-cancer chemotherapy sensitizer prepared by the method of Formulation Example 1 was intratumorally injected under ultrasonographic guidance. Four courses of anti-cancer chemotherapy sensitization were implemented, and the existence and size of the tumors were confirmed by PET-CT at two weeks after the 4 courses of anti-cancer chemotherapy sensitization.

PET-CT images of the patients taken before and after the anti-cancer chemotherapy sensitization are shown in FIGS. 5 and 6 respectively, with the image on the left side in each figure being the PET-CT image before the anti-cancer chemotherapy sensitization, and the image on the right side being the PET-CT image after the anti-cancer chemotherapy sensitization. As can be seen from these, the breast cancer and axillary lymph nodes metastases (indicated by the arrows) have been disappeared by the anti-cancer chemotherapy sensitization of the invention.

These results show that a pronounced treatment sensitizer effect is obtained by using the anti-cancer chemotherapy sensitizer of the invention in combination with the anti-cancer chemotherapy.

BRIEF DESCRIPTION OF THE DRAWINGS

FIG. 1 at the upper left is an image showing the malignant melanoma area prior to radiotherapy, FIG. 1 at the upper right is an image showing the malignant melanoma area at the end of sensitized irradiation (48 Gy), FIG. 1 at the lower left is an image showing the malignant melanoma area two weeks after the end of the radiosensitization therapy, and FIG. 1 at the lower right is an image showing the malignant melanoma area three months after the end of the radiosensitization therapy.

FIG. 2 on the upper-left is an image showing the blood-flow signals in the tumor after irradiation (total dose of 24 Gy) of the malignant fibrous histiocytoma without injection of a radiosensitizer, FIG. 2 on the upper right and 2 on the lower left are images showing blood-flow signals in the tumor after the histiocytoma is injected with a radiosensitizer and irradiated (upper-right FIG. 2: total dose of 36 Gy, lower-left Figure: total dose of 48 Gy), and FIG. 2 on the lower right is an image showing the blood-flow signals in the tumor one week after the end of the radiotherapy.

FIG. 3 on the left is an image showing the right side of the patient's chest, from the thorax to the neck region, FIG. 3 on the upper right is a coronal image of the part obtained by computerized tomography (CT), and FIG. 3 on the lower right is a PET-CT frontal image of the patient.

FIG. 4 on the upper left is a CT image of the neck area prior to radiotherapy, and FIG. 4 on the lower left is a CT image of the right axilla prior to radiotherapy. FIG. 4 on the upper right is a CT image taken after the neck has been irradiated seven times (total dose of 19.25 Gy) without injecting a radiosensitizer, and FIG. 4 on the lower right is a CT image taken after the right axilla has been injected with a radiosensitizer and irradiated seven times (total dose of 19.25 Gy).

Figure 1:
FIG. 1 shows the effect of the radiosensitization method of a malignant melanoma conducted in Reference Example 1.
Figure 2:
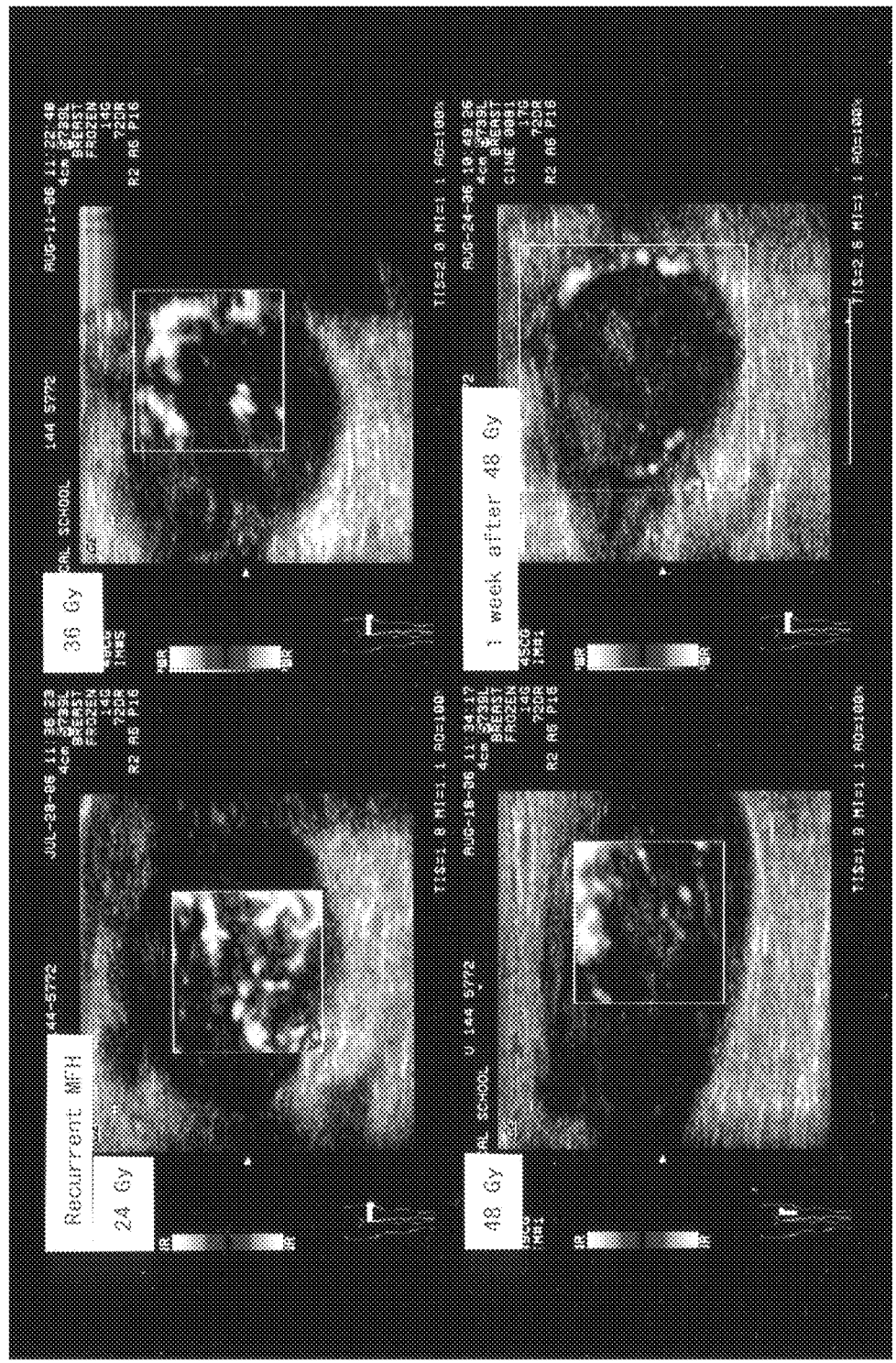
FIG. 2 shows the effect of the radiosensitization method of a malignant fibrous histiocytoma conducted in Example 2.
Figure 3:
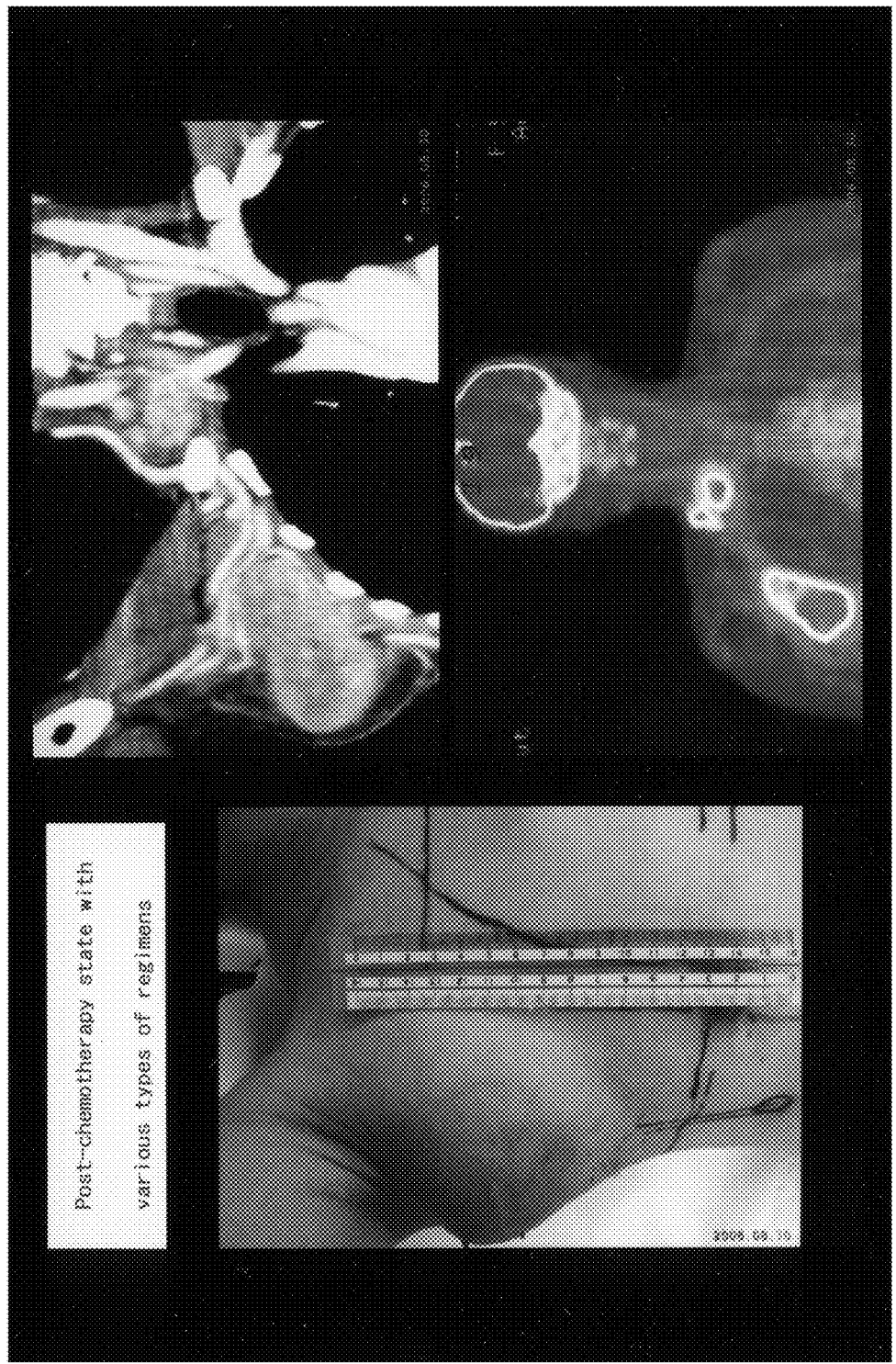
FIG. 3 shows an example of the use of the radiosensitizer of Example 3.
Figure 4:
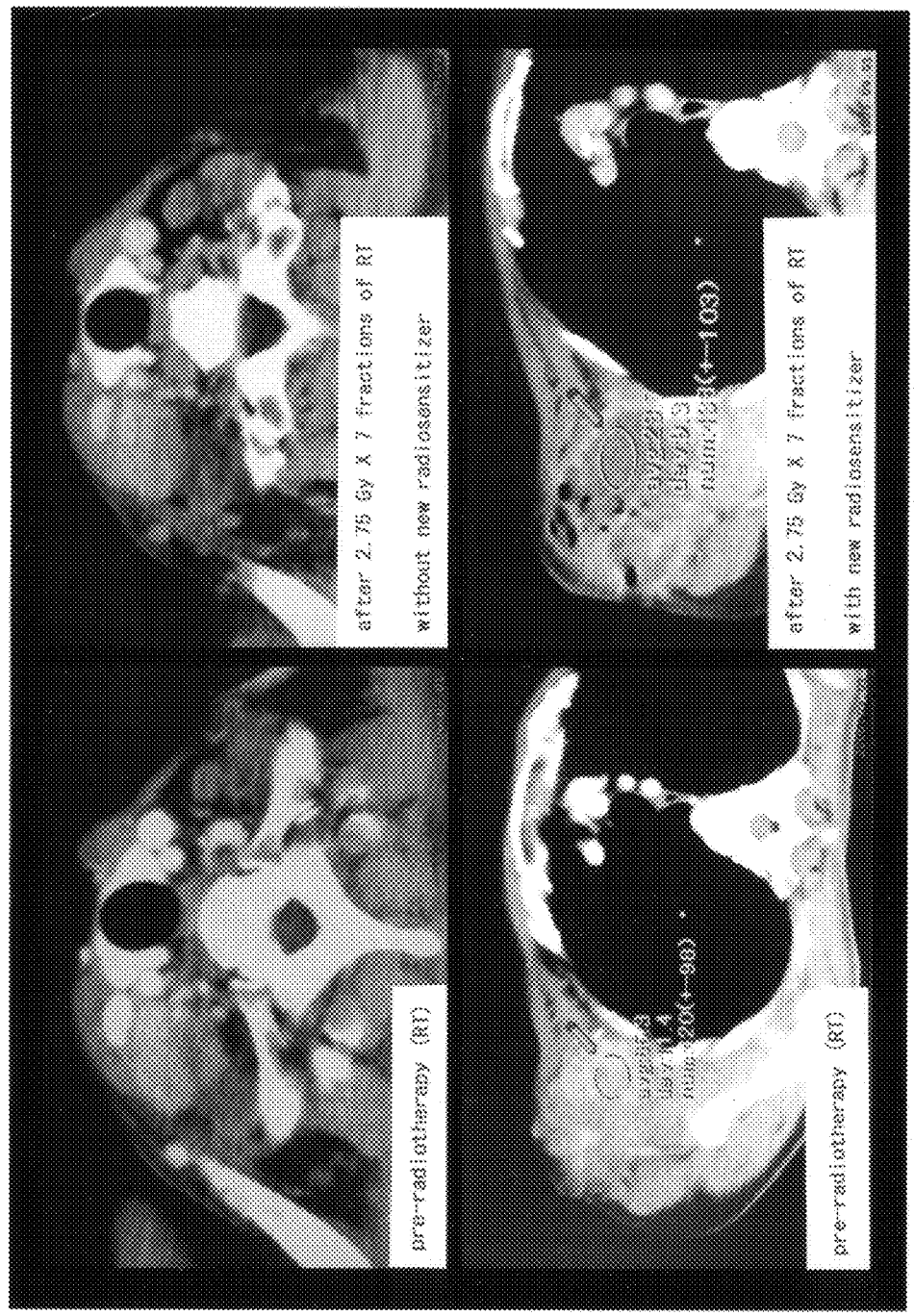
FIG. 4 shows the effect of the radiosensitization method conducted in Example 3.
Figure 5:
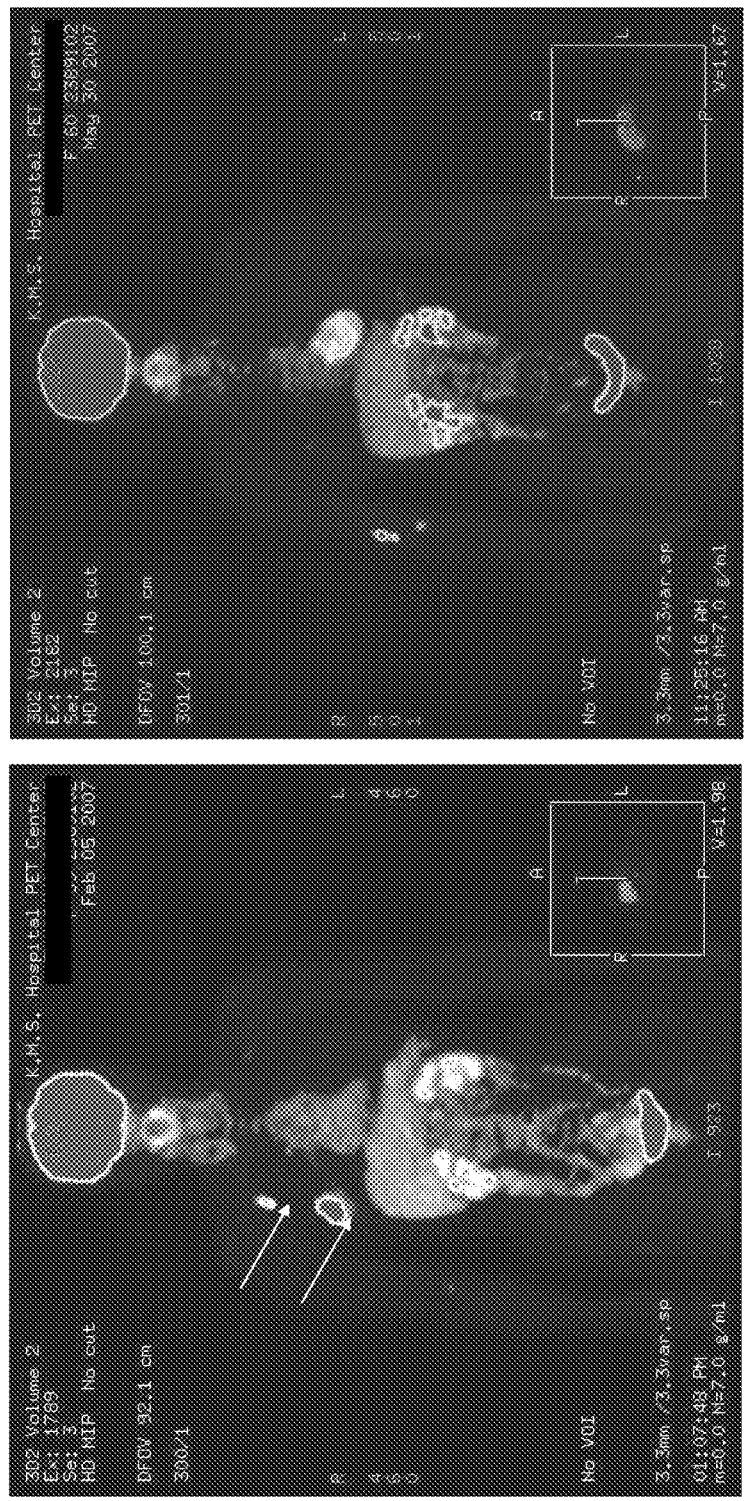
FIG. 5 shows the effect of the anti-cancer chemotherapy sensitization conducted in Example 4. The left side shows a CT image taken prior to anti-cancer chemotherapy sensitization, and the right side shows a CT image taken after anti-cancer chemotherapy sensitization.
Figure 6:
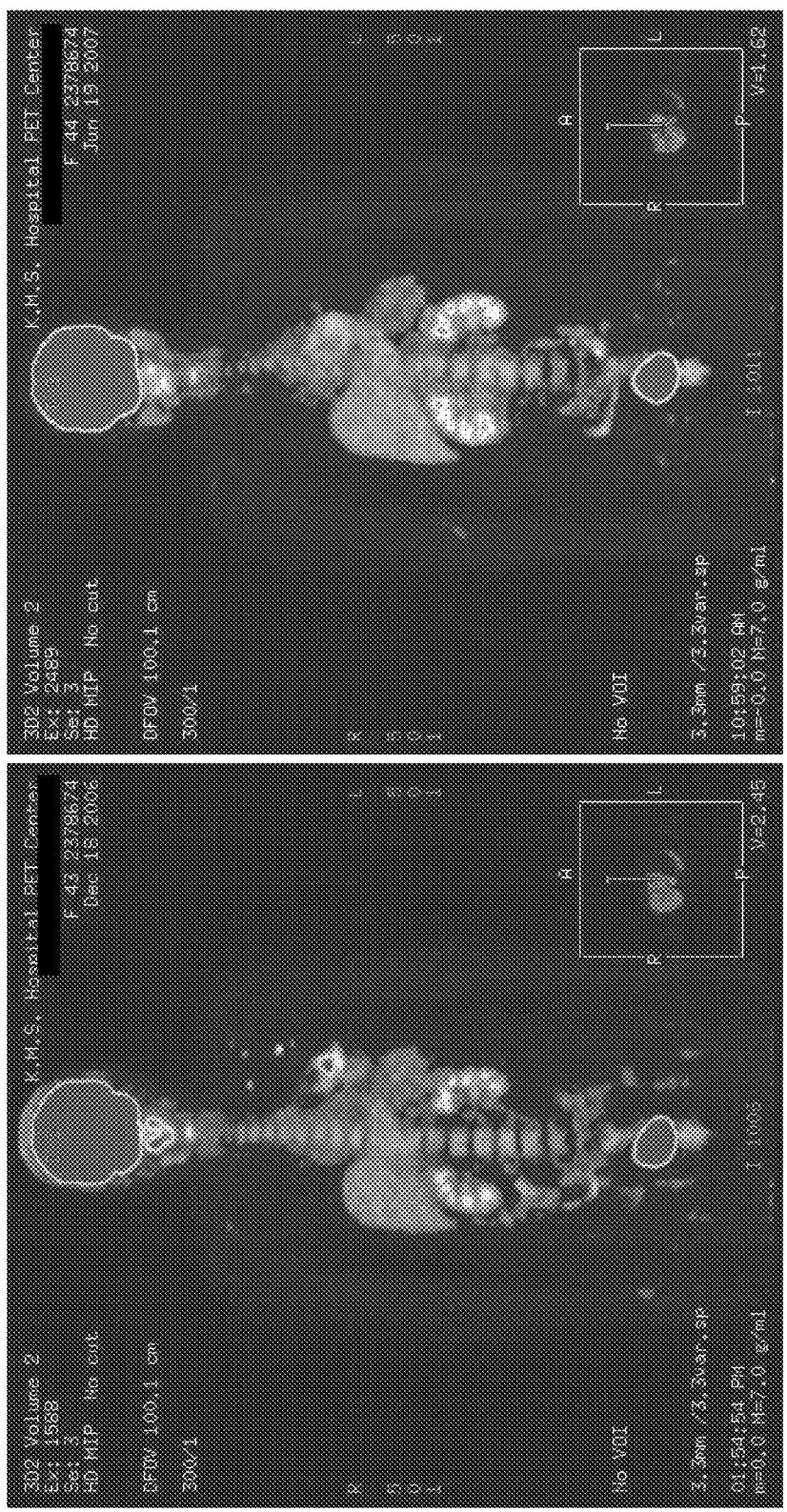
FIG. 6 shows the effect of the anti-cancer chemotherapy sensitization conducted in Example 4. The left side shows a CT image taken prior to anti-cancer chemotherapy sensitization, and the right side shows a CT image taken after anti-cancer chemotherapy sensitization.

The invention claimed is:

1. A method of treating cancer in a patient comprising:
    (1) a step of applying to a tumor a composition comprising (a) 0.1 to 2 weight percent of hydrogen peroxide in a final formulation and (b) hyaluronic acid or a salt thereof, wherein applying the composition is an intratumoral injection, and the tumor is at least one selected from the group consisting of breast cancer and metastatic breast cancer in a lymph node, and
    (2) a step of performing a radiotherapy treatment or an anti-cancer chemotherapy treatment at the same time as or after the step (1),
    wherein the composition delays or reduces degradation of the hydrogen peroxide in the tumor and reduces irritation of the hydrogen peroxide at the time of the injection.

2. The method of treating cancer according to claim 1, wherein the tumor is resistant to the radiotherapy treatment or resistant to the anti-cancer chemotherapy treatment.

3. The method of treating cancer according to claim 1, wherein the radiotherapy treatment is performed and comprises irradiation with an X-ray beam or electron beam from a linear accelerator.

4. The method of treating cancer according to claim 1, wherein the anti-cancer chemotherapy treatment is performed and comprises administering an anti-cancer agent to the patient.

5. The method of treating cancer according to claim 1, wherein a content of the hyaluronic acid or a salt thereof in a final formulation of the composition is 0.1 to 10 weight percent.

6. The method according to claim 1, wherein the concentration of the hydrogen peroxide in the final formulation is 0.36 to 2 weight percent.

7. The method according to claim 1, wherein the intratumoral injection of the composition comprises guidance from an ultrasonographic examination while observing a state of permeation of the composition into the tumor.

8. The method according to claim 1, wherein the composition consists of (a) 0.1 to 2 weight percent of hydrogen peroxide in a final formulation, (b) hyaluronic acid or a salt thereof, and optionally (c) at least one component selected form the group consisting of water, L-methionine, sodium chloride, sodium hydrogenphosphate, crystalline sodium dihydrogen phosphate, glycerin, glucose, polyethylene glycol, propylene glycol, D-mannitol, fructose, xylitol, sodium dihydrogen phosphate, sodium phosphate, hydrochloric acid, sodium hydroxide, a phosphoric acid buffer solution, a tris buffer solution, and an acetic acid buffer solution.

\* \* \* \* \*